United States Patent [19]

Rind

[11] 4,365,625
[45] Dec. 28, 1982

[54] EXPANDABLE ORAL AIRWAY

[76] Inventor: Bruce Rind, 706 NE. 8th Ave., Aberdeen, S. Dak. 57401

[21] Appl. No.: 255,395

[22] Filed: Apr. 20, 1981

Related U.S. Application Data

[63] Continuation-in-part of Ser. No. 188,172, Sep. 17, 1980.

[51] Int. Cl.³ .................... A61M 16/00; A61M 29/00
[52] U.S. Cl. ............................. 128/207.14; 128/345
[58] Field of Search .................... 128/207.14, 200.26, 128/341, 345, 17, 18, 19, 20, 15, 12, 10

[56] References Cited

U.S. PATENT DOCUMENTS

| | | | |
|---|---|---|---|
| 1,097,978 | 5/1914 | Johnson | 128/17 |
| 1,275,520 | 8/1918 | Bell | 128/341 |
| 3,470,872 | 10/1969 | Grieshaber | 128/17 |
| 3,575,163 | 4/1971 | Gasper | 128/17 |
| 3,636,954 | 1/1972 | Weston | 128/321 |
| 4,263,898 | 4/1981 | Wannag | 128/17 |

Primary Examiner—Henry J. Recla
Attorney, Agent, or Firm—Sprung, Horn, Kramer & Woods

[57] ABSTRACT

An expandable airway has two elongated airway forming members having a curved one end portion for effecting insertion and removal of the one end portion of both into and out of the throat of a user and with one member configured to be disposed below the other member. The two members are connected for pivotal movement in response to a force applied at the other end portions of the members from a contracted state to at least one expanded state, wherein the one end portions are spaced apart relative to the contracted state. A mechanism is disposed on the other end portions of the two members for releasably maintaining the members in the at least one expanded state. The other end portions of the two elongated airway forming members have straight sections and the connection comprises a hinge at the straight sections including a first hinge element hingedly connected between the airway forming members and substantially perpendicular to both when the airway is in the contracted state and a second hinge element hingedly connected diagonally between the airway forming members and disposed between the first hinge element and the mechanism for releasably maintaining and spaced apart therefrom, wherein the spacing between the first and second hinge elements is greater at said one airway forming member.

9 Claims, 4 Drawing Figures

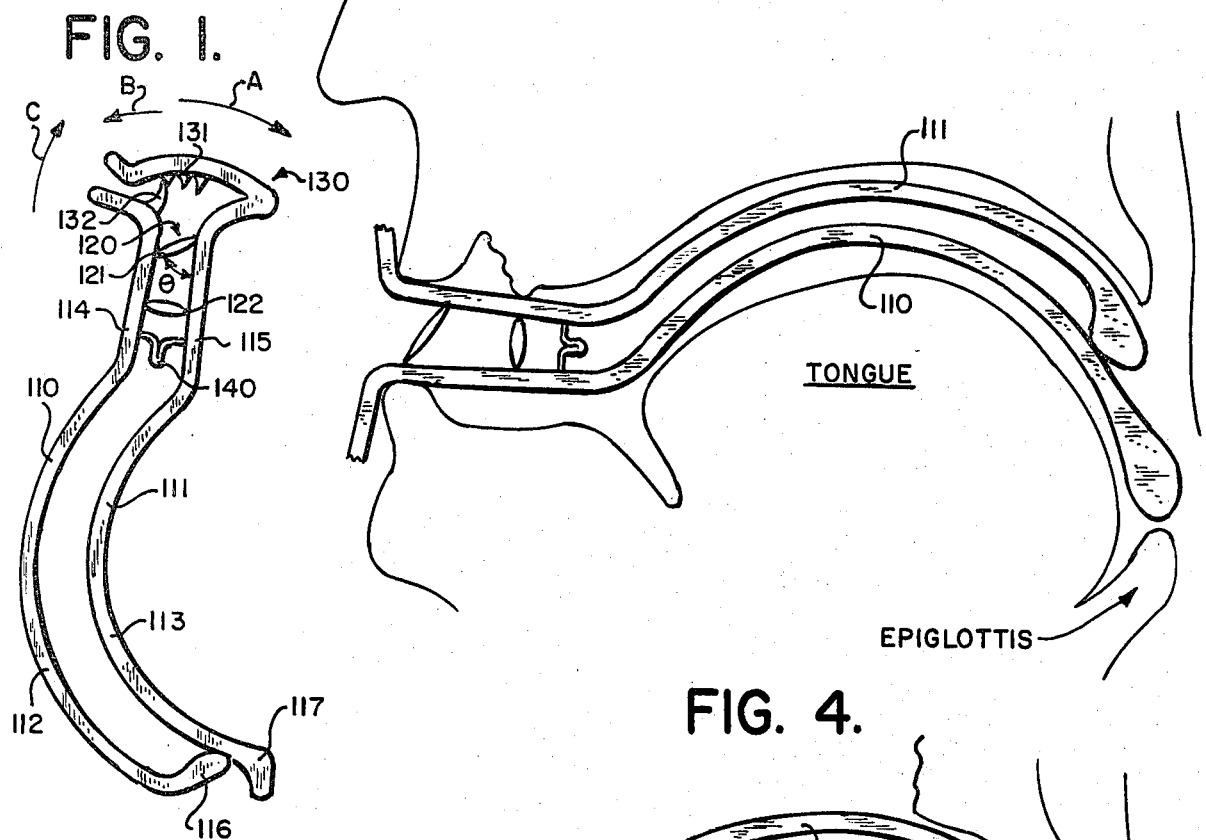
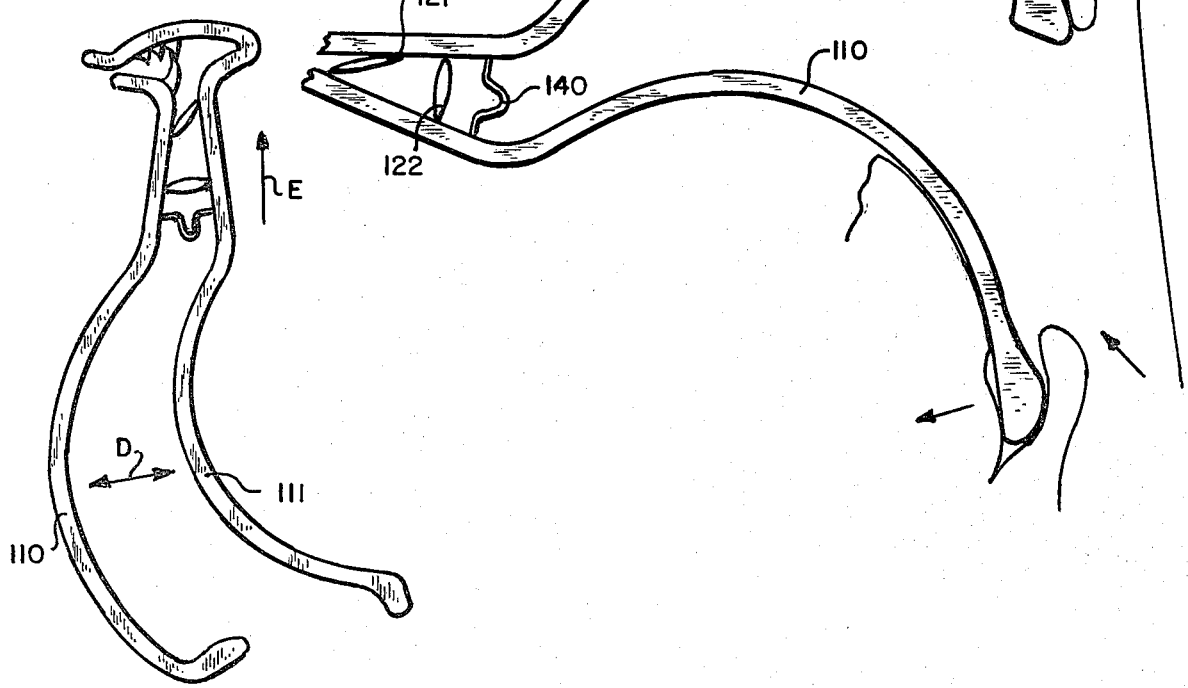

EXPANDABLE ORAL AIRWAY

The present application is a continuation-in-part application of copending application Ser. No. 188,172 filed on Sept. 17, 1980.

BACKGROUND OF THE INVENTION

The present invention relates to an improvement in an expandable airway which is a respiratory medical device for insertion in the mouth and pharynx to provide a passageway extending from a point adjacent to the tracheal orifice through the mouth opening through which air may enter and be expelled in breathing. An airway is particularly useful during surgery when a patient is under an anesthetic or in other situations where a person is unconscious by reason of which the pharynx is collapsed or obstructed so as to prevent natural respiration.

Conventional airways are generally of two types, a first type as disclosed in U.S. Pat. No. 2,599,521 constitutes a unitary member which is not adjustable in size, shape or contour and is made of a substantially rigid member which cannot be altered in use to fit particular patients, particular problems or particular changes in patient condition or position. A second is that shown from example in U.S. Pat Nos. 2,127,215 and 3,930,507 which are adjustable and thus provide for expansion after insertion in the pharynx so as to tailor the device to a particular patient.

The aforementioned adjustable devices and the adjustable specula disclosed in U.S. Pat. Nos. 291,071, 350,809, 883,106, 1,388,421, 1,587,897 and 2,476,675, all have the disadvantage of not permitting an almost instantaneous and fail-safe removal of the airway during an emergency situation, since the mechanisms therefor are complex in nature and require a substantial amount of time for release. The adjustable airway disclosed in U.S. Pat. No. 3,930,507, while permitting a sliding motion to release same, also suffers from the problems of contracting unintentionally as a result of involuntary contractions on the part of the patient.

In my aforementioned copending application, an airway is disclosed which is easily insertable into the pharynx of a patient and which acts not only to depress the tongue, but is able to simultaneously place traction or pressure at the base (cephalad portion) to effect anterior motion of the epiglottis so as to open the air pressure for ventilation with a mask and for the insertion of an endotracheal tube or the like. This prevents a valve-like action of the epiglottis above the larynx which would result in an obstruction when air is forced in the direction of inhalation.

SUMMARY OF THE INVENTION

The main object of the present invention is to provide an improvement in the hinging structure of the expandable airway to effect an improved expansion with simultaneous traction or pressure at the base of the tongue.

These and other objects of the present invention are achieved in the expandable airway according to the present invention having a hinge between the two elongated airway forming members formed from a two hinge elements which enable the airway to effect the simultaneous depression of the tongue and the placing of traction at the cephalad base of the epiglottis to effect an anterior motion or a flipping of the epiglottis. The hinge brings about both relative rotation and longitudinal displacement of the two members according to the invention by comprising a first hinge element hingedly connected between the airway forming members and substantially perpendicular to both when the airway is in the contracted state and a second hinge element hingedly connected diagonally between the airway forming members and disposed between the first hinge element and the means for releasably maintaining and spaced apart therefrom, wherein the spacing between the first and second hinge elements is greater at said one airway forming member.

In a particular advantageous commercial embodiment of the present invention, the members comprise plastic material and the hinge elements form an integral plastic hinge connected between the two members and integral therewith.

These and other objects and advantages of the invention will become apparent when viewed with the drawings which show various embodiments of the invention by way of example wherein:

BRIEF DESCRIPTION OF THE DRAWINGS

FIG. 1 is a side view of one embodiment according to the present invention;

FIG. 2 is a side view of the embodiment of FIG. 1 in an expanded state;

FIG. 3 shows the embodiment of FIGS. 1 and 2 in an expanded state in the mouth; and FIG. 4 shows the airway of FIGS. 1 and 2 in an expanded state in the mouth.

DETAILED DESCRIPTION OF THE INVENTION

Referring now to FIGS. 1 and 2, a first embodiment of the present invention is shown. The airway comprises airway forming members 110, 111 which are pivotally connected by means 120. The members 110, 111 include a substantially arcuate first section 112, 113 which conforms to the shape of the pharynx, straight portions 114, 115 and end portions 116, 117. As shown in FIG. 1, the end portion 117 has an oppositely curved portion which curves towards the member 110 so as to gradually taper and abut end portion 116 of member 110 when the airway is in the contracted state shown in FIG. 1.

The members 110, 111 comprise substantially planar members in the curved configuration and can be made out of a metal or out of a substantially rigid plastic. As a result of the configuration of members 110 and 111, these members form an airway therebetween and when put into the expanded state shown in FIG. 2, provide an entirely unobstructed path from the mouth orifice.

The pivotal connecting means 120 in the embodiment shown in FIGS. 1 and 2 comprises a first hinge element 122 hingedly connected between the airway forming members 110, 111 and substantially perpendicular to both, at the straight portions thereof 114, 115, when the airway is in the contracted state shown in FIG. 1. The connecting means 120 also includes a second hinge element 121 which is hingedly connected diagonally between the airway forming members 110, 111 and disposed between the first hinge element 122 and maintaining means 130. The second hinging element 121 is disposed at an angle $\theta$ with respect to airway forming 111, there $\theta$ is about 30° to 60° and is preferably 45° when the airway is in the contracted state.

While the hinge elements 121, 122 can be hingedly connected to the airway forming members by conventional techniques, in a particularly advantageous commercial embodiment the members 121, 122 are formed from the same plastic material as the airway forming members 110, 111 and form an integral plastic hinge therewith at the connecting portions. The members 121, 122 have relatively thick central portions and thin web portions where they integrally connect with members 110, 111.

The hinge enables a unique relative movement between the airway forming members 110, 111 such that there is an expansion movement to increase the distance at the curved portions thereof to a distance D shown in FIG. 2 and at the same time to laterally shift the two airway forming members in a direction E. Specifically, the airway forming member 111 which is configured to be disposed below airway forming member 110 when inserted in the throat, moves outwardly when pivoted so as to effect the simultaneous depression of the tongue and the anterior pulling at the base of the tongue to pull and thereby elevate the epiglottis in order to further clear the treachea. This is clearly illustrated in FIGS. 3 and 4.

The members 110 and 111 are shown in the contracted state in FIG. 1 with the end portions 116, 117 preferably abutting and tapered to the termini thereof so as to enable the easy insertion of the airway into the pharynx. Since during the use of the airway it is desirable to adjust the size of the airway to the particular patient or a particular condition of a patient, the members 110 and 111 are pivotable about the hinge to move from the contracted state shown in FIG. 1 to any one of a plurality of expanded states as for example shown in FIG. 2. In order to maintain the members 110, 111 in the expanded state, a maintaining means 130 is provided. The maintaining means 130 includes a portion 131 on member 110 and a portion 132 on member 110. More specifically, the maintaining means comprises a ratchet mechanism with the portion 132 comprising means forming a pawl and the portion 131 forming ratchet teeth which preferably increase progressively in length. The pawl engages with the individual ratchet teeth so as to slide in direction A without any resistance, however it locks in direction B as a result of the engagement of the pawl and a given ratchet tooth. The means forming the ratchet mechanism are preferably elastically deformable in a direction C which is substantially the direction of removal of the device from the pharynx. The deformation of the portion 131 in response of the removal of the airway in the direction C, acts to release the pawl from the teeth thus permitting the airway to move from the expanded state shown in FIG. 2 to the contracted state shown in FIG. 1 and thus enable the removal thereof without any further manipulations.

The termini 116, 117 preferably diverge from the curve of the arcuate portions of the members 110, 111 so that the portion 116 abuts member 111 when the device is in the contracted state and the portion 117 slightly overlaps portion 116 so as to form a tapering configuration to enable the ease of insertion into the pharynx. Moreover, the end portions 116, 117 are preferably rounded at their tips and have a widened end portion to prevent tissue damage during insertion. Finally, portion 117 is configured to favorably act on the base of the tongue so as to more reliably effect the elevation of the epiglottis during expansion.

FIGS. 3 and 4 show the insertion of the embodiment of the invention shown in FIGS. 1 and 2 in the pharynx. FIG. 3 shows the insertion of the device and its position in the pharynx in the contracted state while FIG. 4 shows the position of the pharynx when the airway is in the expanded state. As can be clearly seen, the longitudinal displacement effected by the novel hinge pulls the base of the tongue so as to elevate the epiglottis and provide a clear path into the treachea.

In order to ensure that the members 110, 111 will return to the contracted state when the maintaining means 130 is released, a spring element 140 is preferably provided between members 110 and 111 and urging them into the contracted state. The spring 130 is preferably made of the same material as the members 110, 111 and is integral therewith.

It will be appreciated that the instant specification and claims are set forth by way of illustration and not limitation, and that various modifications and changes may be made without departing from the spirit and scope of the present invention.

What is claimed is:

1. In an expandable oral airway having two elongated airway forming members each having a curved one end portion adapted to fit the contours of the mouth and pharnyx of a throat of a patient for effecting insertion and removal of the one end portion of both into and out of the throat of a user and with one member configured to be disposed below the other member, means connecting the two members for pivotal movement in response to a force applied at the other end portions of the members from a contracted state to at least one expanded state, wherein the one end portions are spaced apart relative to the contracted state and holding means disposed on the other end portion of one of said members for releasably holding the other of said members such that the members are maintained in said at least one expanded state, the improvement wherein each other end portion of the two elongated airway forming members has a straight section, said straight sections being substantially parallel and in spaced apart relation and wherein the connecting means comprises hinge means at the straight sections including a first rigid element hingedly connected to each airway forming member and substantially perpendicular to both when the airway is in the contracted state and a second rigid element hingedly connected to each airway forming member and extending diagonally therebetween, said second rigid element being disposed between the first rigid element and said holding means and wherein the spacing between the hinge connections of said first and second rigid elements to said airway members is greater at said one airway forming member.

2. The airway according to claim 1, wherein the airway forming members and rigid elements comprise plastic material.

3. The airway according to claim 2, wherein the rigid elements form an integral plastic hinge between the airway forming members.

4. The airway according to claim 1, wherein the second rigid element is disposed at an angle of from about 30° to 60° with respect to the one airway forming member when the airway is in the contracted state.

5. The airway according to claim 4, wherein the second rigid element is at an angle of 45° with respect to the one airway forming member when the airway is in the contracted state.

6. The airway according to claim 1, wherein the members are pivotable to a plurality of expanded states and the maintaining means releasably maintains the members in any one of the plurality of expanded states at a given time.

7. The airway according to claim 2, wherein the maintaining means comprises a one-way ratchet mechanism including first means forming progressively longer ratchet teeth on one member and second means forming a pawl on the other member engageable therewith and wherein at least one of the first and second means is elastically deformable in response to a force in the removal direction to release the ratchet mechanism.

8. The airway according to claim 1, wherein the one end portions of the two members are configured in the closed state to be gradually closer towards the termini thereof.

9. The airway according to claim 1, wherein the termini of the two members abut in the contracted state.

* * * * *